US010668301B2

(12) United States Patent
Vinh-Hung et al.

(10) Patent No.: US 10,668,301 B2
(45) Date of Patent: Jun. 2, 2020

(54) CALIBRATION OF RADIATION THERAPY TREATMENT PLANS FOR A SYSTEM

(71) Applicants: Vincent Vinh-Hung, Fort-de-France (FR); Nam P. Nguyen, Washington, DC (US)

(72) Inventors: Vincent Vinh-Hung, Fort-de-France (FR); Nam P. Nguyen, Washington, DC (US)

(*) Notice: Subject to any disclaimer, the term of this patent is extended or adjusted under 35 U.S.C. 154(b) by 22 days.

(21) Appl. No.: 16/033,101

(22) Filed: Jul. 11, 2018

(65) Prior Publication Data

US 2019/0015683 A1  Jan. 17, 2019

Related U.S. Application Data

(60) Provisional application No. 62/608,751, filed on Dec. 21, 2017, provisional application No. 62/531,073, filed on Jul. 11, 2017.

(51) Int. Cl.
*A61N 5/10* (2006.01)
*A61B 6/00* (2006.01)

(52) U.S. Cl.
CPC ............ *A61N 5/1031* (2013.01); *A61B 6/463* (2013.01); *A61B 6/502* (2013.01); *A61N 5/1071* (2013.01)

(58) Field of Classification Search
CPC ............... A61N 5/1031; A61N 5/1071
See application file for complete search history.

(56) References Cited

U.S. PATENT DOCUMENTS

| 5,511,549 | A | 4/1996 | Legg et al. |
| 8,064,642 | B2 | 11/2011 | Sheng et al. |
| 2005/0111621 | A1* | 5/2005 | Riker ................... A61N 5/1031 378/65 |
| 2013/0083004 | A1* | 4/2013 | Nord .................... A61N 5/1031 345/419 |
| 2013/0197878 | A1 | 8/2013 | Fiege et al. |
| 2013/0217948 | A1 | 8/2013 | Mihaylov |
| 2013/0324784 | A1 | 12/2013 | Fredriksson et al. |

OTHER PUBLICATIONS

Viggars et al. The Objective Evaluation of Alternative Treatment Plans III: The Quantitative Analysis of Dose Volume Histograms. Int. J. Radiation Oncology Biol. Phys. vol. 23, No. 2, 1992, pp. 419-427.
Katie Sharkey and Jothybasu Selvaraj, Dose-Volume Histogram Calculation in Radiotherapy Treatment Plans Using VTK. Oct. 9, 2012 Tags: The Source Issue 23, VTK. https://blog.kitware.com/dosevolumehistogramcalculationinradiotherapytreatmentplansusingvtk/.
International Search Report for PCT Application No. PCT/US18/41697 dated Nov. 14, 2018.

* cited by examiner

*Primary Examiner* — Chih-Cheng Kao

(57) ABSTRACT

A simple metric, the mean absolute dose deviation ("MADD"), for characterizing dose-volume histograms ("DVH") is disclosed. The MADD facilitates the use and the comparison of DVHs. The MADD is defined as the average of absolute differences between all points of a DVH and a dose point of a specified reference dose range. The MADD is a generalized metric free from distribution assumptions, and it is directly applicable to all types of structures.

14 Claims, 13 Drawing Sheets

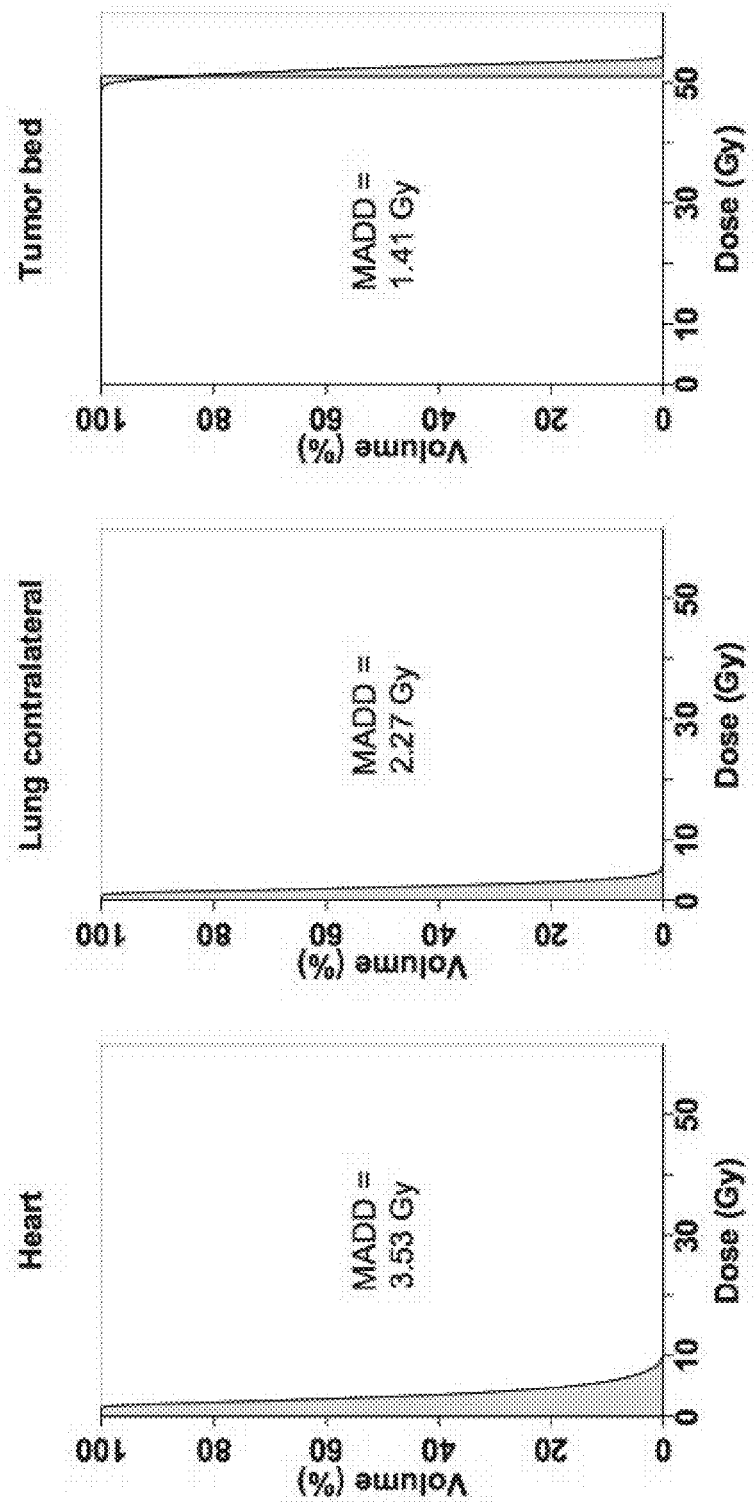

Calculate, for each data point comprising the DVH, an absolute value of a difference between the dose value and the reference dose
101

Compute, for each data point comprising the DVH, a product of the absolute value calculated and a volume step (between successive volume values of a given axis of the DVH)
102

Acquire an absolute dose deviation for each data point comprising the DVH by dividing the product computed by a total volume of the structure of interest
103

Determining the mean absolute dose deviation by computing a summation of the absolute deviation of all data points
104

Refining the radiation treatment plan based on the mean absolute dose deviation
105

FIG. 6

Calculate, for each data point comprising the DVH, an absolute value of a difference between the dose value and a dose point of a specified dose range for a structure
201

Compute, for each data point comprising the DVH, a product of the absolute value calculated and a volume step (between successive volume values of a given axis of the DVH)
202

Acquire an absolute dose deviation for each data point comprising the DVH by dividing the product computed by a total volume of the structure of interest
203

Determining the mean absolute dose deviation by computing a summation of the absolute deviation of all data points for all dose points of the specified range
204

Decompose the mean absolute dose deviation as a sum a mean absolute dose deviation pertaining to excess dose and a mean absolute dose deviation pertaining to insufficient dose
205

Refining the radiation treatment plan based on the decomposed mean absolute dose deviation
206

FIG. 9

CALIBRATION OF RADIATION THERAPY TREATMENT PLANS FOR A SYSTEM

CROSS REFERENCE

This application claims priority to U.S. Provisional Patent Application No. 62/608,751, filed Dec. 21, 2017, and to U.S. Provisional Patent Application No. 62/531,073, filed Jul. 11, 2017, the specifications of which are incorporated herein in their entirety by reference.

FIELD OF THE INVENTION

The present invention relates to calibration of radiation therapy treatment plans using dose-volume histograms, more specifically, to a common metric for analyzing the efficacy of dose-volume histograms.

BACKGROUND OF THE INVENTION

A dose-volume histogram ("DVH") is a graphical summary output from a radiation treatment planning that summarizes the distribution of the computed radiation doses delivered to a given structure. The most frequently used type of DVH is the cumulative DVH. Unless otherwise specified, a DVH without other mention refers to the cumulative DVH. Usually by convention the ordinate, y-axis, represents the structure's volume as a percentage or as a proportion (relative volume), and the abscissa, x-axis, represents the absolute dose. The DVH plots the volume receiving a dose greater than or equal to the corresponding dose represented on the x-axis. The DVH curve displays on the ordinate axis the percent or fraction volume of the structure irradiated in excess of the dose specified on the abscissa.

The major utility of the DVH is to evaluate whether a treatment plan would be associated with excess toxicity and/or with inadequate dose to control a tumor. Sets of DVH constraints and specifications of dose-volume requirements can be defined prior to conducting a radiation treatment plan. Comparison of the DVH between different treatment plan alternatives is a cornerstone in the radiation treatment planning process. International recommendations specify selected DVH points for reporting patients' treatment plans, such as the $D_{mean}/D_{min}/D_{max}$, i.e., the mean/minimum/maximum dose received by a structure, respectively. Or $D_{2\%}$, $D_{50\%}$, $D_{95\%}$, $D_{98\%}$, the dose received by 2%, 50%, 95%, 98% of the volume of the structure, respectively.

In the constructed example of FIG. 1A, the $D_{95\%}$ would be found by drawing a horizontal line at the volume y=0.95, locating its intersection with the curve, and reading the vertical projection on the x-axis, which in this case is 32.8 Gy. Hence, the report would say $D_{95\%}$=32.8 Gy. Alternative ways of reporting can, equivalently, use volume-dose points such as $V_{20\ Gy}$ or $D_{95\%}$, i.e., the volume of the structure receiving in excess of 20 Gy or in excess of 95% of the prescribed dose, respectively. Reading the $V_{xx}$ mirrors reading the $D_{yy}$. In FIG. 1A, where the prescribed dose is 50 Gy, the $V_{20\ Gy}$ equals 1 (100% of the volume), and the $D_{95\%}$ corresponds to $V_{47.5\ Gy}$ (47.5 Gy is 95% of 50 Gy), which from the curve equates 0.5, i.e., 50% of the volume.

Except for $D_{mean}$, the various doses $D_{yy}$ or volumes $V_{xx}$ presented above are selected points of the DVH curve for a structure. These points might or might not be representative of the DVH curve. Rather than focusing on selected dose-volume points, the present invention considers how the full DVH curve differs from a given dose A specified as reference. The difference is measured as the area between the actual DVH and the specified dose A. Herein, the specified dose A is a single dose value, for example a prescription of a uniform dose of 50 Gy to the structure. The does A may be any user-specified set of doses or dose-range, for example the prescription of a dose varying from 40 to 60 Gy to the structure. Since the difference can be in excess or in lack, which could generate negative area values, the absolute value of the deviation is used. This area is herein referred to as the mean absolute dose deviation ("MADD") of the DVH from the dose A.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a method of characterizing a DVH evaluating a radiation treatment plan for controlling a tumor associated with a structure of interest. This characterization is acquired by determining the MADD of a plurality of data points comprising the DVH from a dose of radiation. Each data point may comprise a dose value and a volume value of the structure. In some embodiments, the method comprises calculating an absolute value of a difference between the dose value of an initial data point and the dose. Herein, the dose may include any user-specified set of doses or dose-range. Following, a product of the previously calculated absolute value and a volume step (between successive volume values of the DVH) is computed. In other embodiments, an absolute dose deviation for the initial data point is acquired by dividing the previously computed product by a total volume of the structure of interest. These steps may then be repeated for each data point (106), and the mean absolute dose deviation is obtained by computing a summation of the absolute deviation of all data points. These steps may further be repeated for a set of several dose points.

Consistent with previous embodiments, determining the mean absolute dose deviation of the DVH from the specified reference dose or a set of several dose range or dose points characterizes the DVH by quantifying a lack of dosage or an excess of dosage of radiation to the structure of interest. In this way, a refined evaluation of the efficacy of the radiation treatment plan is provided.

The MADD is a new DVH metric. It was required that the new metric 1) be consistently applicable to organs at risk as well as to target volumes, and 2) be physically meaningful. Various metrics have been described in current technology. However, either said metrics defined different measures for organs and targets, or were not physical measures but probabilistic scores. Metrics are often expressed in different scales with different measurement units. It can be confusing to compare a homogeneity index or a conformity index, which are abstract numbers without physical dimension, with a Dyy or to a Vxx, which are physical doses and volumes. The present invention provides a coherent measure fulfilling the requirements of applicability and physical consistency. Additionally, the present invention makes a distinction between under dosage and over dosage. There might arise situations in which specific information on insufficient and excess dose would be useful, or in which the user might be interested only in one component. An example is the analysis of the outcome of cancer treatments, when the user wants to analyze how the rate of tumor recurrence relates with insufficient dosage, or, conversely, how the rate of complication relates with over dosage. Thus, the present invention includes a method of decomposition of the MADD.

The concept of the area relative to the DVH has been previously proposed in literature. The term "histogram of regret" once designated portions of the area between the DVH and the prescribed dose to targets. The area under the DVH has also been known to represent the mean dose. Absolute deviations have also been used in current technology. However, these earlier studies did not generalize the concept, and no unified formal proof was presented. With regard to the separation of excess and insufficient doses, there has been attempts to present a visual display based on various coloring schemes for diverse sub-regions of dose volume histograms (Viggars, Shalev, Stewart, and Hahn, 1992). However, this was an empirical presentation without a physical basis, no unifying metric tool was provided.

BRIEF DESCRIPTION OF THE DRAWINGS

The features and advantages of the present invention will become apparent from a consideration of the following detailed description presented in connection with the accompanying drawings in which:

FIG. 4A shows the MADD for a heart in a case of breast cancer.

FIG. 4B shows the MADD for a contralateral lung in a case of breast cancer.

FIG. 4C shows the MADD for a tumor bed in a case of breast cancer.

FIG. 6 shows a flowchart of an embodiment of the present invention.

FIG. 9 shows a flowchart of an embodiment of the present invention.

DETAILED DESCRIPTION OF THE INVENTION

Figure 1A:
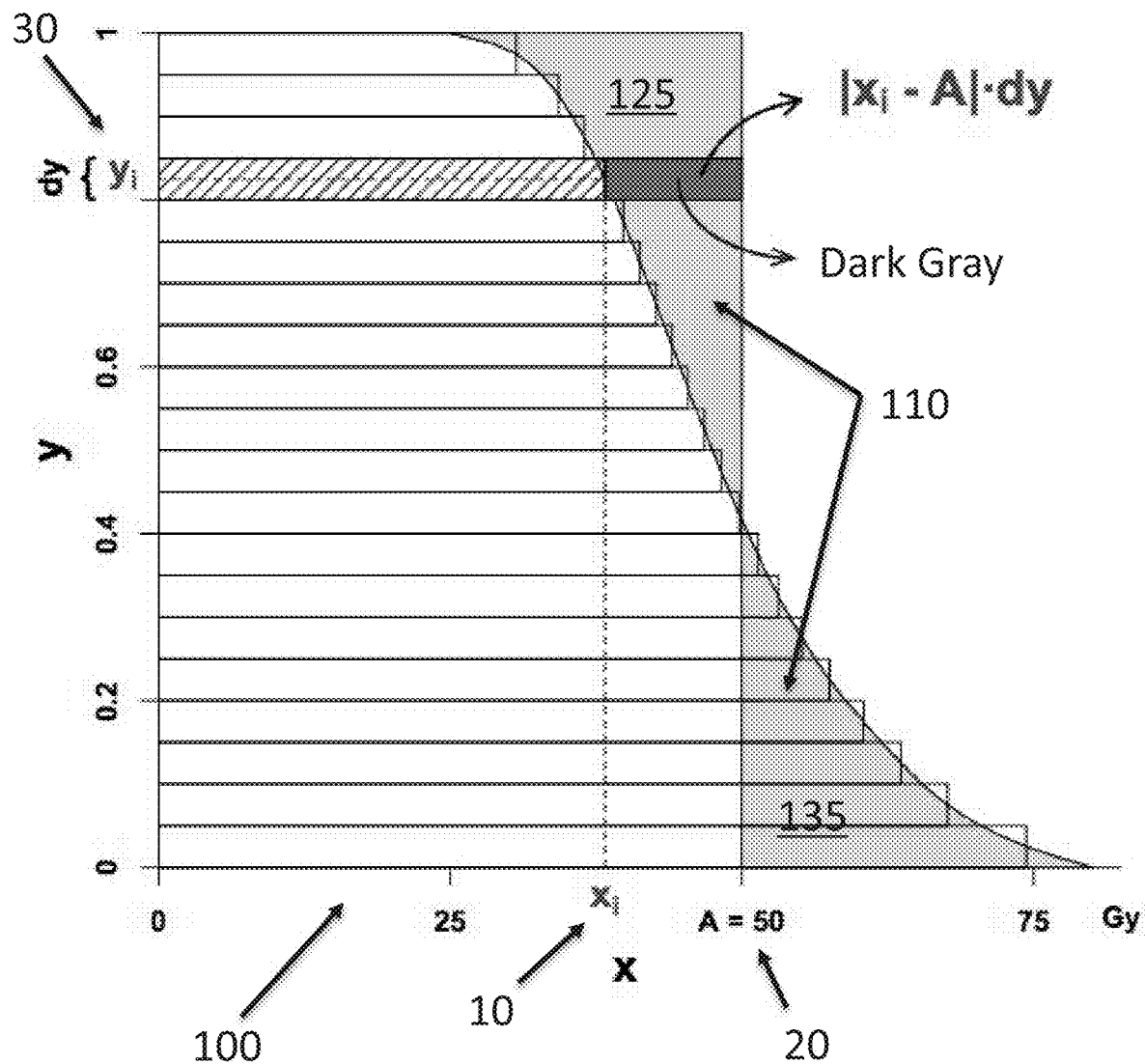
FIG. 1A shows a constructed dose-volume histogram (DVH) curve for a target structure, an actual dose applied (striped bar), an absolute deviation of the DVH from the prescribed dose A (dark gray bar is lack of dose applied). The mean absolute deviation from dose A is shown in the area shaded grey.
Figure 1B:
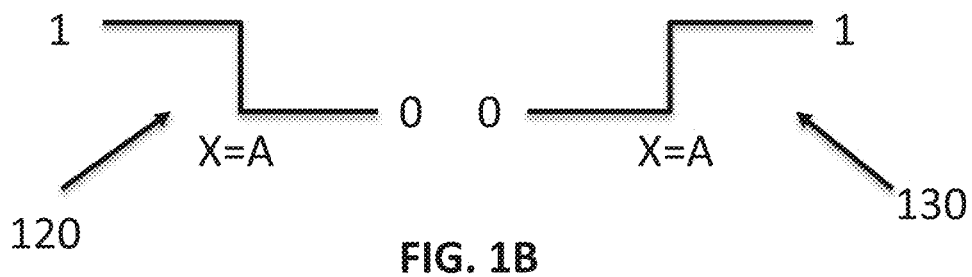
FIG. 1B shows a step function $I_{insufficient}$, and a step function $I_{excess}$.
Figure 1C:
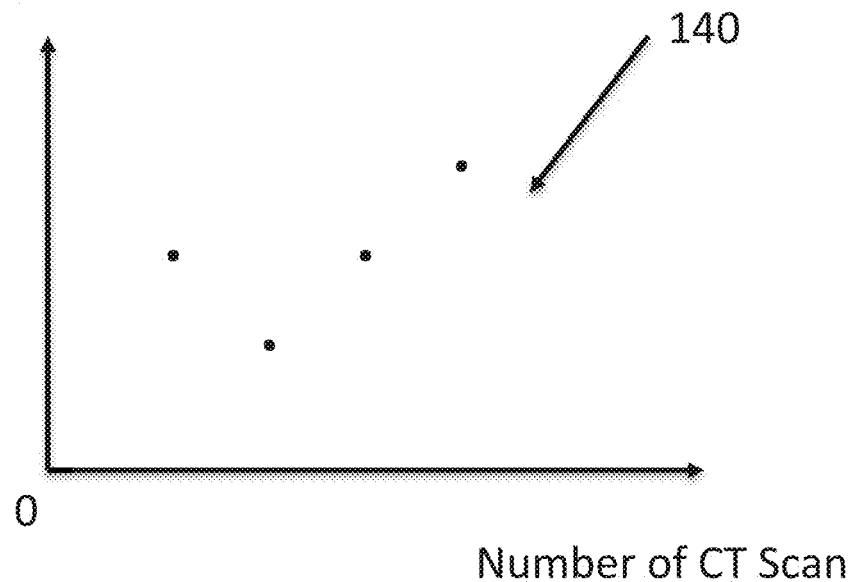
FIG. 1C shows a plot of $M(A_{MIN})$ per number of CT scans.
Figure 1D:
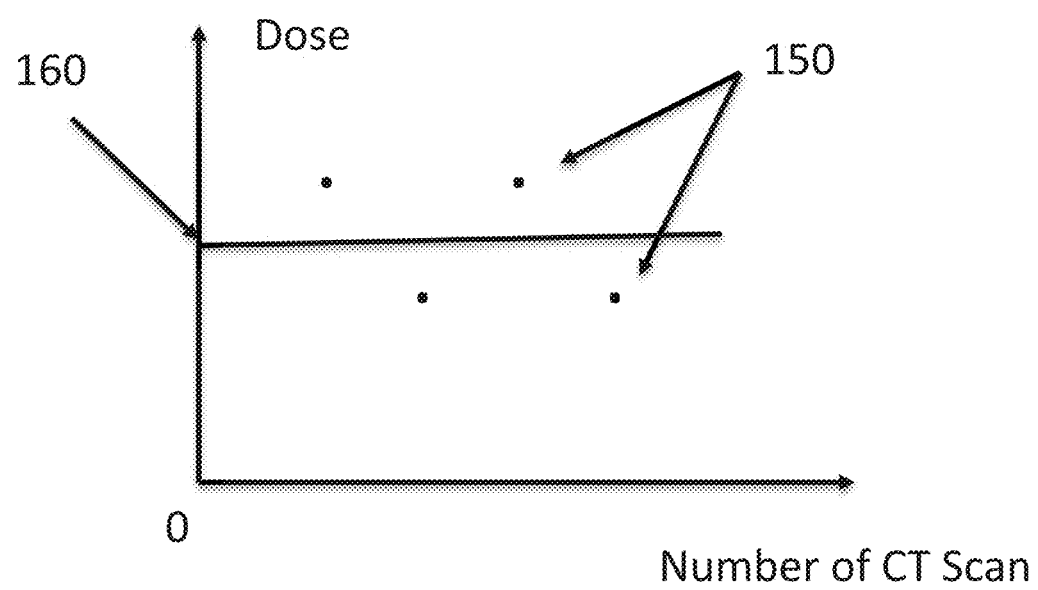
FIG. 1D shows a plot of applicable dose per number of CT scans.
Figure 1E:
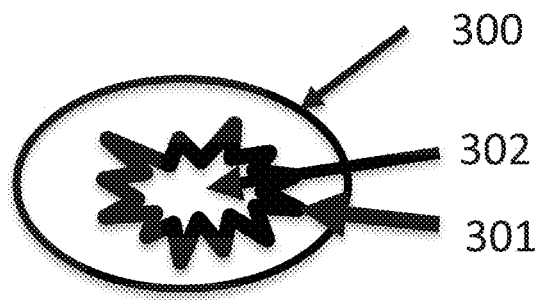
FIG. 1E shows a structure of a patient with an at-risk organ and a tumor.
Figure 1F:
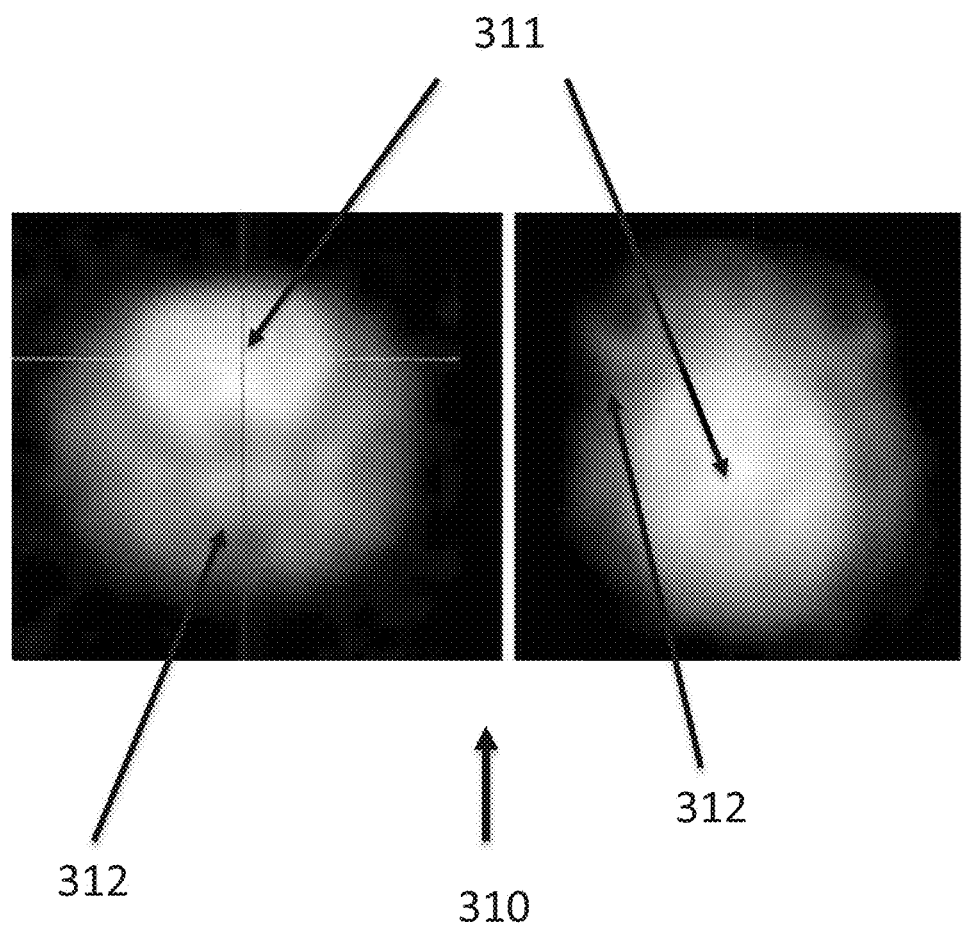
FIG. 1F shows two two-dimensional image slices (310) of a tumor target volume (311) and a non-target structure volume (312).
Figure 1G:
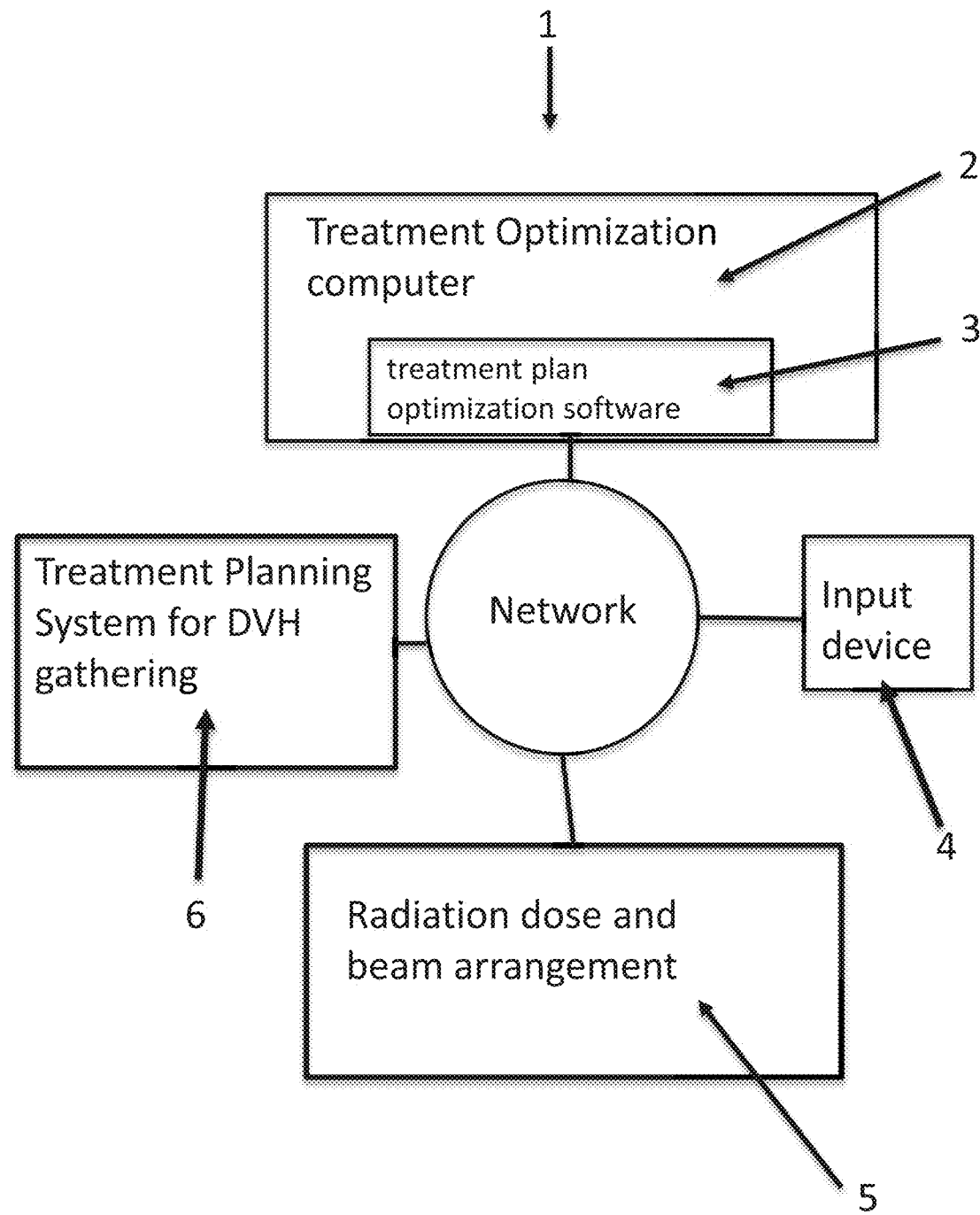
FIG. 1G shows a system of determining an optimal dose in a beam arrangement for treating a tumor.

Referring now to FIGS. 1A-9, in one embodiment, the present invention features a method for enabling calibration of a dose delivery of a radiotherapy treatment plan. As a non-limiting example, the method may comprise: providing a dose-volume histogram (DVH) (100) of the treatment plan for a structure (300) with a volume $V_0$, and a reference dose A (20), the DVH comprising a plurality (n) of data points, each data point comprising a dose of radiation $x_i$ (10) corresponding to a percentage of volume $\delta y_i$ (30); determining a calibration parameter M(A) (110), based on the DVH (100), to quantify the dose delivery of the treatment plan, wherein the M(A) (110) is calculated using the following equation:

$$M(A) = \sum_{i=1}^{n} \frac{|x_i - A| \times \delta y_i}{V_0};$$

and refining the treatment plan based on said calculated M(A) value. In preferred embodiments, the calibration of the treatment plan may be separate from administration of the treatment plan to a patient. As a non-limiting example, calibration of the treatment plan may be done before treatment of a patient with the calibrated treatment plan. As a further non-limiting example, the treatment plan may include treating a patient with a plurality of radiotherapy doses, wherein each dose has a specified location and intensity.

According to some embodiments, the treatment plan may be calibrated for treatment of a patient in need thereof. As non-limiting examples, the treatment plan may be calibrated for treatment of a tumor or a cancer. In one embodiment, the treatment plan may be refined by comparing the M(A) to a reference value; and revising the treatment plan if the M(A) is above the reference value, determining a new M(A) for the revised treatment plan, and repeating the steps until the calibration parameter is below the reference value. As a non-liming example, the reference value may be about 0.1, 0.2, 0.3, 0.4, 0.5, 0.6, 0.7, 0.8, 0.9, 1, 1.2, 1.4, 1.6, 1.7, 1.8, 2, 2.25, 2.5, 2.75, 3, 3.5, 4, 5, 6, 7, 8, 9 or 10. As a further non-liming example, the reference value may be about a range of 0.01-0.1, 0.1-0.2, 0.2-0.3, -0.3-0.4, 0.4-0.5, 0.5-0.6, 0.6-0.7, 0.7-0.8, 0.8-0.9, 0.9-1, 1-1.2, 1.2-1.4, 1.4-1.6, 1.6-1.8, 1.8-2, 2-2.25, 2.25-2.5, 2.5-2.75, 2.75-3, 3-3.5, 3.5-4, 4-5, 5-6, 6-7, 7-8, 8-9 or 9-10. In another embodiment the treatment plan may be revised by searching for $A_{min}$ (150) by adjusting parameters of the treatment plan, wherein $M(A_{min})$ (140) is a minimum value.

In preferred embodiments, the treatment plan may be refined to minimize both insufficient dosage and excess dosage. In an embodiment, the method may further comprise identifying an amount of insufficient dosage (125) by multiplying M(A) with a step function $I_{insufficient}$ (120), wherein:

$$I_{insufficient}(x) = \begin{cases} 1 & \text{if } x \leq A \\ 0 & \text{if } x > A \end{cases}$$

In another embodiment, the method may further comprise identifying an amount of excess dosage (135) by multiplying M(A) with a step function $I_{excess}$ (130), wherein:

$$I_{excess}(x) = \begin{cases} 0 & \text{if } x \leq A \\ 1 & \text{if } x > A \end{cases}$$

According to another embodiment, the present invention may feature a system (1) for enabling calibration of a radiation therapy treatment plan for a tumor (302) within a structure (300) of a patient, and identifying an optimal dose in a beam arrangement to prevent excess radiation to an at-risk organ (301) of the patient. In one embodiment, the system may include a treatment plan optimization computer (2) having a memory to store data and treatment plan optimization software (3). In another embodiment, the system may have an input device (4) in communication with the treatment plan optimization computer (2) and software (3) to provide user access to control functions of the treatment plan optimization software (3). In still another embodiment, the system may include a graphical user interface to display an at least two-dimensional image slice (310) of the tumor target volume (311) and the non-target structure volume (312), graphical objects, and graphical representations of radiation dose distribution calculated for each iteration of the proposed dose and radiation beam arrangement overlaid upon the displayed image slice. In preferred embodiments, the determination of the optimal dose is separate from administration of the radiation therapy treatment plan using the optimal dose In yet another embodiment, the treatment plan optimization software (3) may include a set of instructions that, when executed by the treatment plan optimization computer (2), causes the computer to perform operations to computationally obtain a proposed radiation dose and beam arrangement (5) and to computationally iteratively optimize the proposed radiation dose in the beam arrangement based on a plurality of constraints to form the optimized radiation dose and beam arrangement.

In a further embodiment, the operations may include receiving inputs from the input device (4) representing direct graphical user manipulation of a graphical representation of radiation dose distribution for a current iteration of the proposed radiation dose and beam arrangement (5) displayed on the graphical user interface, and responsive to user manipulation of the displayed graphical representation of radiation dose distribution for the current iteration of the proposed radiation dose and beam arrangement. In a still further embodiment, the operations may include computationally obtaining and providing data to graphically display a graphical representation of radiation dose distribution for a next iteration of the proposed radiation dose and beam arrangement which substantially realizes the graphically altered radiation dose distribution, to thereby iteratively form the optimized radiation dose and beam arrangement.

According to one embodiment, the operation of computationally obtaining and providing data may include obtaining a dose-volume histogram (DVH) (100) of the structure (300) from a computerized "Treatment Planning System" (TPS) (6). In some embodiments, the DVH may vary according to several parameters, such as a topography of the at-risk organs, a topography of the tumor, constraints of dose to the organ that should not be exceeded and so on. According to another embodiment, the operation of computationally obtaining and providing data may include providing a mean absolute dose deviation (MADD) (110) based on the (DVH) (100), wherein the MADD (110), or M(A), is calculated using the following equation:

$$M(A) = \sum_{i=1}^{n} \frac{|x_i - A| \times \delta y_i}{V_0}$$

wherein $x_i$ (10) is a dose corresponding to a percentage of volume $\delta y_i$ (30), A is a reference dose (20), $V_0$ is the volume of interested structure, and the calculation process is done by a computer with an input dose of A.

According to still another embodiment, the operation of computationally obtaining and providing data may include identifying an amount of either an insufficient dosage or an excess dosage by multiplying M(A) with a step function. According to even another embodiment, the operation of computationally obtaining and providing data may include finding an applicable dose $A_{min}$ (150) for the DVH (100) by searching for $A_{min}$ wherein $M(A_{min})$ (140) reaches minimum value for the DVH (100).

In some embodiments, the operation of finding $A_{min}$ may comprise: obtaining a series of DVH(j) by adjusting parameters for DVH (100) for the structure (300) of the patient, wherein j is at least 1; finding a series of applicable dose $A_{min}$ (j) (150) by calculating a series (j) of $M(A_{min})$ (j) (140) for each DVH(j); and identifying an optimal dose $A_0$ (160) that has minimum standard deviation (SD) for a series of applicable dose (150) from the obtained $M(A_{min})$ (j) (140). In other embodiments, the optimal dose $A_0$ (160) may be the base for an optimal treatment plan for the tumor (302) in the radiation therapy, or the least amount of radiation received by an at-risk organ (301) when the structure (300) is under treatment.

In one embodiment, all dose points of the specified dose range may be input by a user. In one other embodiment, two or more dose points of the specified range are input by a user, and remaining dose points of the specified range are computed using interpolation. In another embodiment, the structure of interest is a target volume of tumor or an organ at risk. In still another embodiment, the specified reference dose may be zero when the structure of interest is an organ at risk. In other embodiments, the partial volume may be either a percentage or a relative proportion of the total volume of the structure of interest. In preferred embodiments, the insufficient dose and the excess dose may be indiscriminately combined to obtain total mean absolute dose deviation.

In other embodiments, the present invention features a method of characterizing a dose-volume histogram ("DVH") to refine a radiation treatment plan evaluated by the DVH, where the radiation treatment plan is for controlling a tumor associated with a structure of interest. Further, the radiation treatment plan may prescribe a specified reference dose of radiation for the structure of interest. Characterization of the DVH is acquired by determining a mean absolute dose deviation ("MADD") of a plurality of data points comprising the DVH from the specified reference dose.

In some embodiments, each data point comprising the DVH comprises a dose of radiation to be received by a partial volume of the structure of interest. The DVH may further comprise a volume step between successive volume values on a given axis of the DVH. In additional embodiments, for each data point, the method comprises:
- calculating the absolute value of the difference between the dose value of radiation and the specified reference dose (102),
- computing the product of the calculated absolute value and the volume step (103),
- acquiring the absolute dose deviation by dividing the computed product by a total volume of the structure of interest (104).

The MADD may then be obtained by computing the summation of the absolute deviation of all data points (105).

Consistent with previous embodiments, determining the MADD of the DVH quantifies a lack or an excess dose of radiation relative to the specified reference dose. Utilizing this information, the radiation treatment plan may be refined (106), where said refining comprises increasing or decreasing the dose of radiation applied to the corresponding partial volume based on the MADD.

In alternate embodiments, the structure of interest may be either a target volume of the tumor or an organ at risk. In an embodiment, the specified reference dose is zero when the structure of interest is the organ at risk.

In some embodiments, the partial volume is a percentage of the total volume of the structure of interest. In other embodiments, the partial volume is a relative proportion of the total volume of the structure of interest.

The method of the present invention may be realized via a system comprising a processor, a memory operatively coupled to the processor, and a user display. The memory may store the DVH and instructions that, when executed by the processor, implement the method.

The present invention also features an alternate representation of the method for characterizing a DVH to refine a radiation treatment plan evaluated by the DVH. In some embodiments, the radiation treatment plan prescribes a specified reference dose, A, for the structure of interest. In further embodiments, the method comprises: creating a 3-dimensional dose distribution image of the structure of interest and constructing the DVH from the 3-dimensional dose distribution image. The DVH may comprise a plurality of data points. In additional embodiments, each data point comprises a dose of radiation, $x_i$, to be received by a partial volume of the structure of interest. The DVH may further comprise a plurality of volume steps, $dy_i$, between successive volume values on a given axis of the DVH.

In supplementary embodiments, the MADD, M(A), is calculated using the following equation:

$$M(A) = \sum_{i=1}^{n} \frac{|x_i - A| \times \delta y_i}{V_0}$$

where n is the number of the data points, and $V_0$ is a total volume of the structure of interest. Calculating the MADD of the DVH quantifies a lack or an excess dose of radiation relative to the specified reference dose, said quantification may be used to refining the radiation treatment plan. The refining may comprise increasing or decreasing the dose of radiation applied to the corresponding partial volume based on the MADD.

The present invention also features an alternate representation of the method for characterizing a DVH to refine a radiation treatment plan evaluated by the DVH. In some embodiments, the radiation treatment plan prescribes a set of user-specified doses or dose range, Ai, for the structure of interest. As described above, the method may include creating a 3-dimensional dose distribution image of the structure of interest and constructing the DVH from the 3-dimensional dose distribution image. The DVH may comprise a plurality of data points. In additional embodiments, each data point comprises a dose of radiation, $x_i$, to be received by a partial volume of the structure of interest. The DVH may further comprise a plurality of volume steps, $dy_i$, between successive volume values on a given axis of the DVH.

The MADD, M(A), is calculated using the following equation:

$$M(A) = \sum_{i=1}^{n} \frac{|x_i - A_i| \times \delta y_i}{V_0}$$

where n is the number of the data points, and $V_0$ is a total volume of the structure of interest.

Discussions of the MADD where A Represents a Single Dose Value

The equation to compute the MADD using discrete DVH data points is:

$$M(A) = \sum_{i=1}^{n} \frac{|x_i - A| \times \delta y_i}{V_0} \quad (1)$$

where $x_i$, $y_i$, i=1 . . . n are the n pairs of DVH dose ($x_i$)—volume ($y_i$) data points outputted by the treatment planning for the structure of interest, $\delta y_i$ are the volume steps between successive points, $V_0$ is the structure's volume (1 if relative proportion, 100 if percentage, or actual absolute volume, according to the choice of volume representation), and A is the dose specified for that structure.

The same equation applies to any type of structure, whether a target volume or an organ at risk. The only requirement is the specification of A. In the case of a target volume, A is the prescribed dose to the target. In the case of an organ at risk or any non-target volume, no radiation dose should be delivered. That requirement of no dose can be explicitly specified as A set to 0.

Discussions of the MADD Where A Represents a Set of Doses or a Dose Range

For a user specified set of doses or dose-range, Ai, equation (1) can be modified as shown below:

$$M(A) = \sum_{i=1}^{n} \frac{|x_i - A_i| \times \delta y_i}{V_0} \quad (7)$$

where $x_i$, $y_i$, i=1 . . . n are the n pairs of DVH dose ($x_i$)—volume ($y_i$) data points outputted by the treatment planning for the structure of interest, $\delta y_i$ are the volume steps between successive points, $V_0$ is the structure's volume or actual absolute volume, according to the choice of volume representation), and $A_i$ is the dose-range specified for that structure.

The case of a single dose value is used when the prescriber wants to deliver the same dose to the whole structure and equation (1) is used to compute the MADD. However, if the prescriber desires to deliver a minimum dose up to a maximum dose to the structure, and when the prescriber considers that any dose within the range is desirable or acceptable, then equation (7) may be used to compute the MADD. Herein, $A_i$ indicates that the computations are performed on a set of several A dose points.

Similar to equation (3), equation (7) can be rewritten on a continuous scale, to explicitly declare A as a function, as shown below:

$$M(A) = \int_0^{V_0} \frac{|x(y) - A(y)|}{V_0} dy \qquad (8)$$

Application Examples

Figure 2:
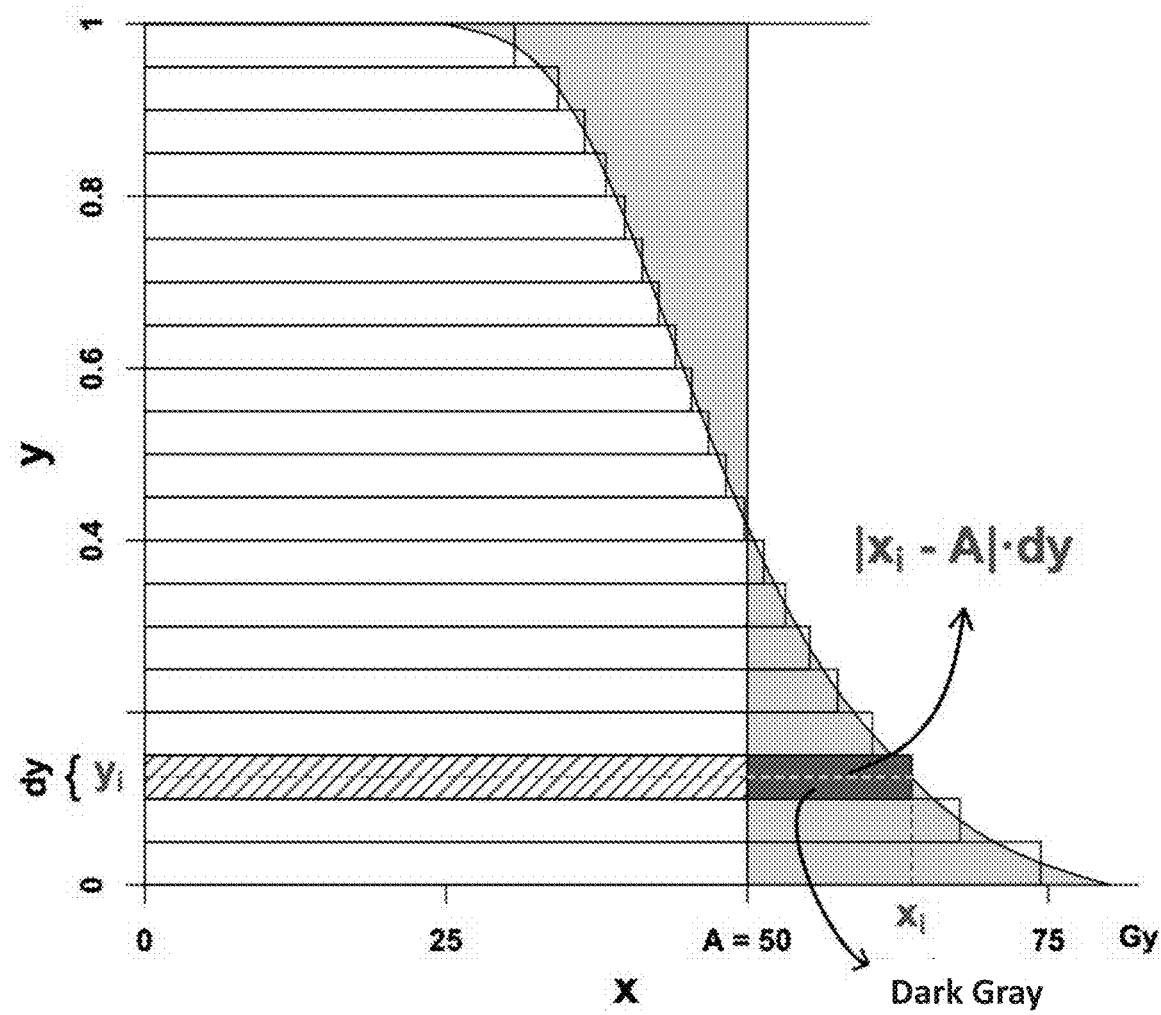
FIG. 2 shows a constructed DVH curve for a target structure, an actual dose applied (striped bar), an absolute deviation of the DVH from the prescribed dose A (dark gray bar is excess of dose applied). The mean absolute deviation from dose A is shown in the area shaded grey.
Figure 3:
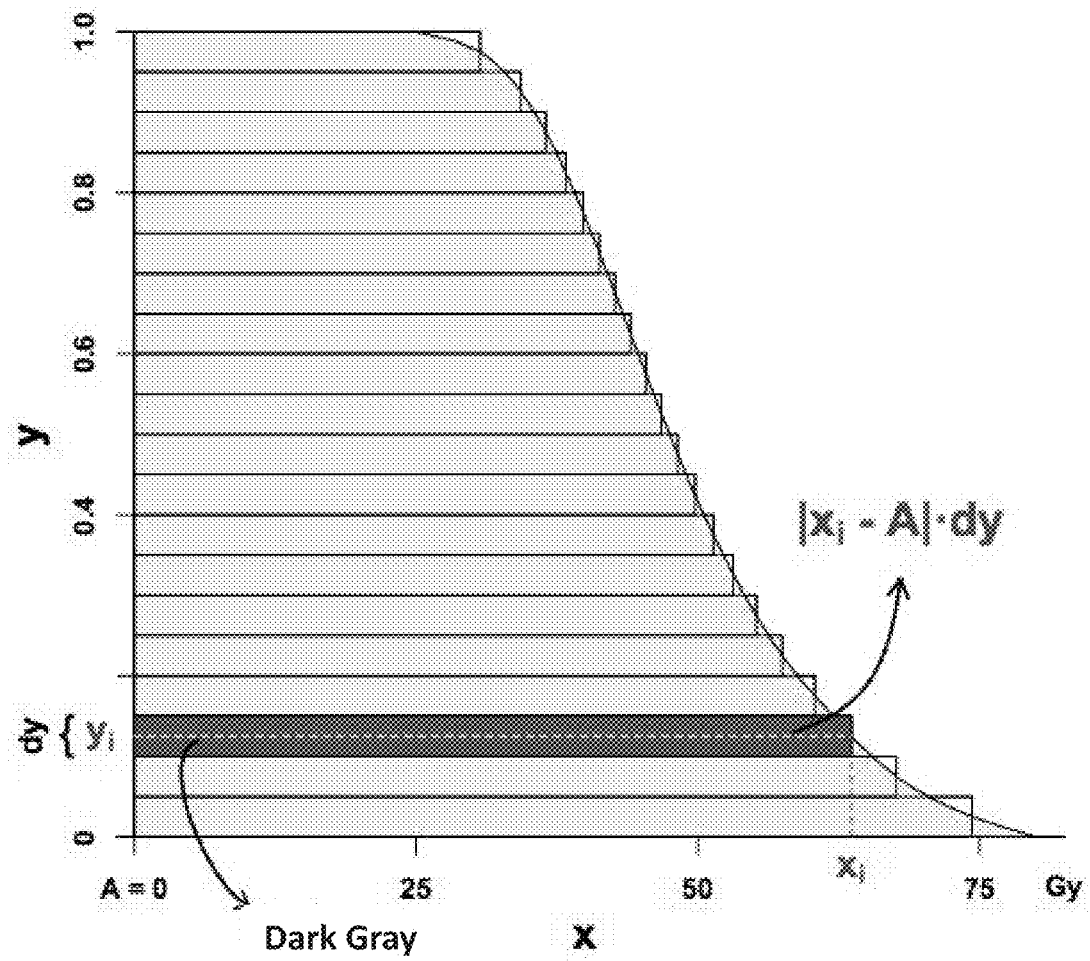
FIG. 3 shows a constructed DVH curve for an organ at risk, an actual dose applied, an absolute deviation of the DVH from the prescribed dose A (dark gray bar is excess of dose applied). The mean absolute deviation from dose A is shown in the area shaded grey, which is equal to the mean dose.
Figure 4F:
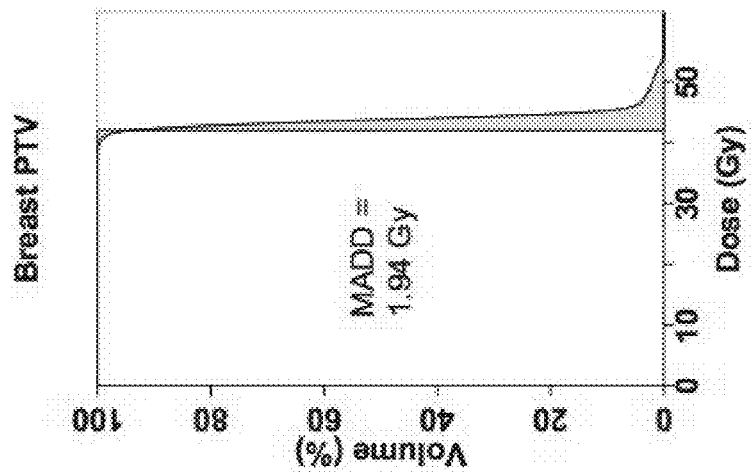
FIG. 4F shows the MADD for a breast planning target volume (PTV) in a case of breast cancer.
Figure 4E:
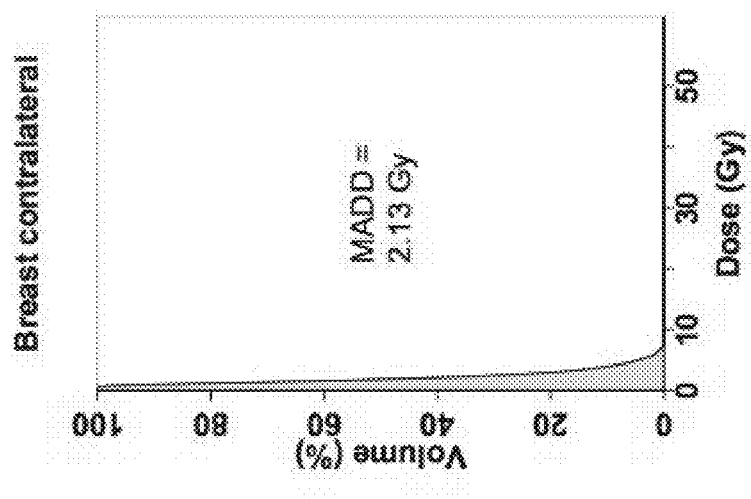
FIG. 4E shows the MADD for a contralateral breast in a case of breast cancer.
Figure 4D:
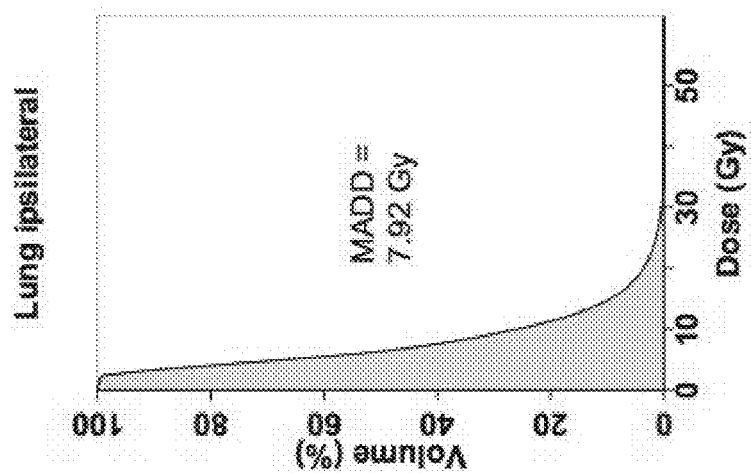
FIG. 4D shows the MADD for an ipsilateral lung in a case of breast cancer.

FIGS. 1A and 2 show the area M (A:A=50 Gy) for a target in which the prescribed dose is 50 Gy, any dose different from 50 Gy is a deviation from the prescription. Note that owing to the use of absolute deviation, there is no dependence on the sign of the deviation. Whether the deviation is a lack of dose (FIG. 1A) or an excess of dose (FIG. 2), the computational procedure is the same. FIG. 3 shows the area M (A:A=0 Gy) for an organ at risk. Note that physically, there can be no negative dose, hence there is no <0 area. Any dose >0 to a non-target structure is an excess dose.

The MADD was applied to the case of a right breast cancer patient receiving post-conserving surgery adjuvant radiation with a volumetric arc technique. The dose prescribed to the breast was 42 Gy over 15 fractions, with a simultaneous integrated boost resulting in a cumulative dose of 51 Gy to the tumor bed. FIGS. 4A-4F shows the DVH for the breast planning target volume ("PTV"), the tumor bed, the heart, the ipsilateral and contralateral lung, and the contralateral breast. This is the actual treatment that the patient received. The planning approval was based on conventional review of DVH and 3-D images. The MADDs for the different structures provide an overall meaningful view of the dose deviations. It can be seen that the breast PTV had a MADD of 1.94 Gy, about 5% of its 42 Gy prescribed dose, almost all of it as excess dose. The tumor bed had a MADD of 1.41 Gy, about 3% of its 51 Gy prescribed dose, almost all excess dose. The ipsilateral lung received a substantial mean dose of 7.92 Gy. In view of the MADD values in this case, further planning could have been requested.

Figure 7:
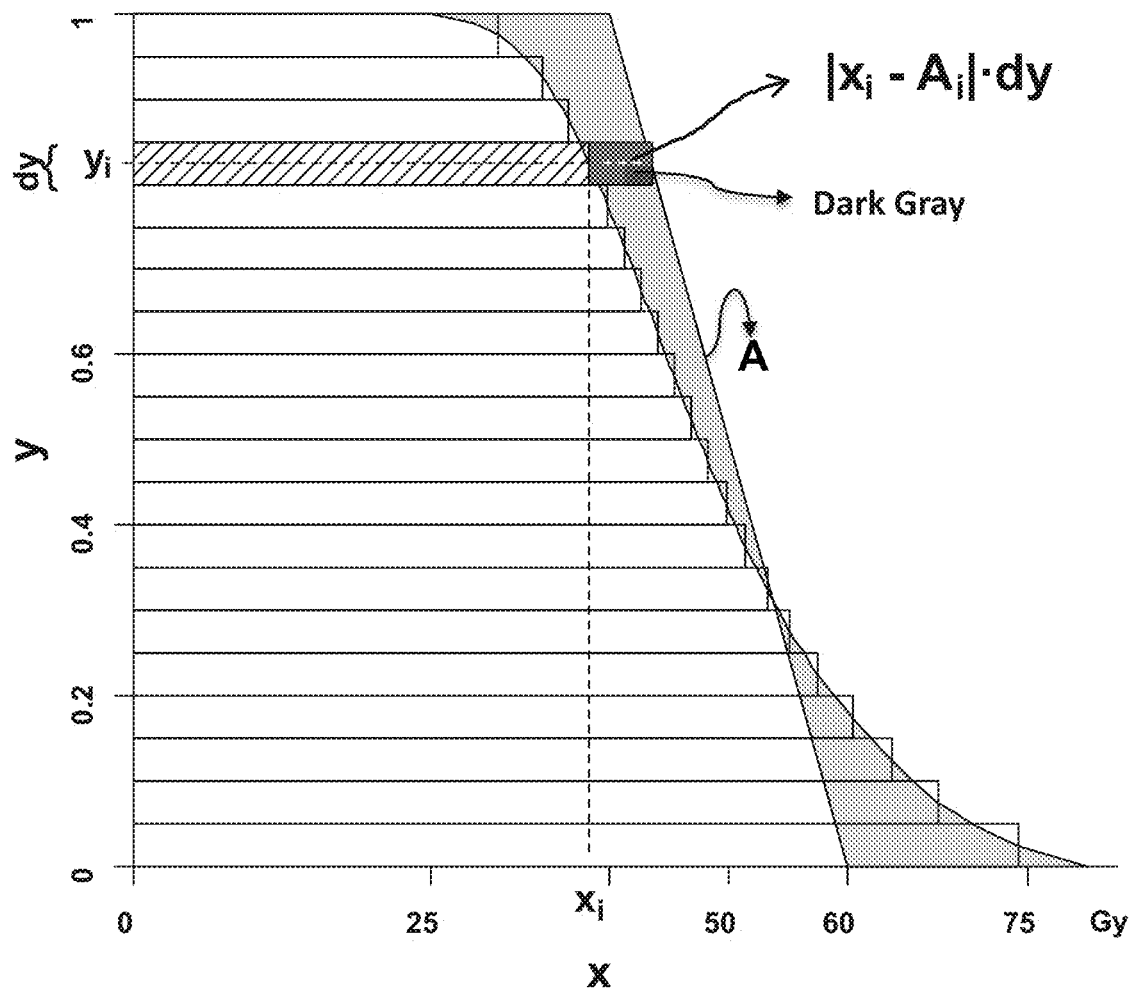
FIG. 7 shows the constructed DVH curve for the target structure having a dose range from 40 Gy to 60 Gy.

FIG. 7 shows an example with the same DVH as in FIG. 1. But instead of a single dose prescription A=50 Gy of FIG. 1, FIG. 7 shoes a dose range from 40 Gy to 60 Gy, which is drawn on the figure as the oblique A line. The mean absolute dose deviation of the DVH relative to the 40-60 Gy prescription is represented by the grey shaded area.

MADD Advantages

The MADD is an easily computable metric. The computation is transparent, which can be particularly helpful when debugging programming scripts. Speed can be an asset when designing Monte Carlo methods. The MADD is free from distributional assumptions. There is no requirement for the DVH to be Gaussian, normal or non-normal. More importantly, the MADD is robust, can help the design of DVH scores, can handle embedded substructures, and can facilitate the interpretation of treatment plans.

Robustness, Versus the Standard Deviation

The MADD is a measure of dispersion. The closest metric to MADD is standard deviation ("SD"), which is routinely reported in treatment planning printouts. The SD is the square root of the variance. The variance Var(x) is the average of the sum of the squares of the deviation of x from its mean $\mu$, where $\mu = \sum_{i=1}^n x_i$:

$$SD = \sqrt{\text{Var}(x)} = \frac{\sqrt{\sum_{i=1}^n (x_i - \mu)^2}}{\sqrt{n}} \qquad (9)$$

Use of the squaring function in variance calculations amplifies the effect of outliers. Use of the square root does not eliminate that distortion. By contrast, the MADD does a simple direct averaging of the deviations, and so is less affected by extremes. This is relevant to radiation therapy. In a radiation dose distribution, outliers are the extreme doses, such as the maximum absorbed dose ($D_{max}$, $D_{0\%}$) or the minimum absorbed dose ($D_{min}$, $D_{100\%}$). The International Commission on Radiation Units and Measurements ("ICRU") questioned the relevance of these extreme dose points and recommended reporting the dose near maximum, $D_{2\%}$, and the dose near minimum, $D_{98\%}$. The SD, in giving more weight to extreme doses, countermands the ICRU recommendation, whereas the MADD would be in line with the ICRU.

Figure 5:
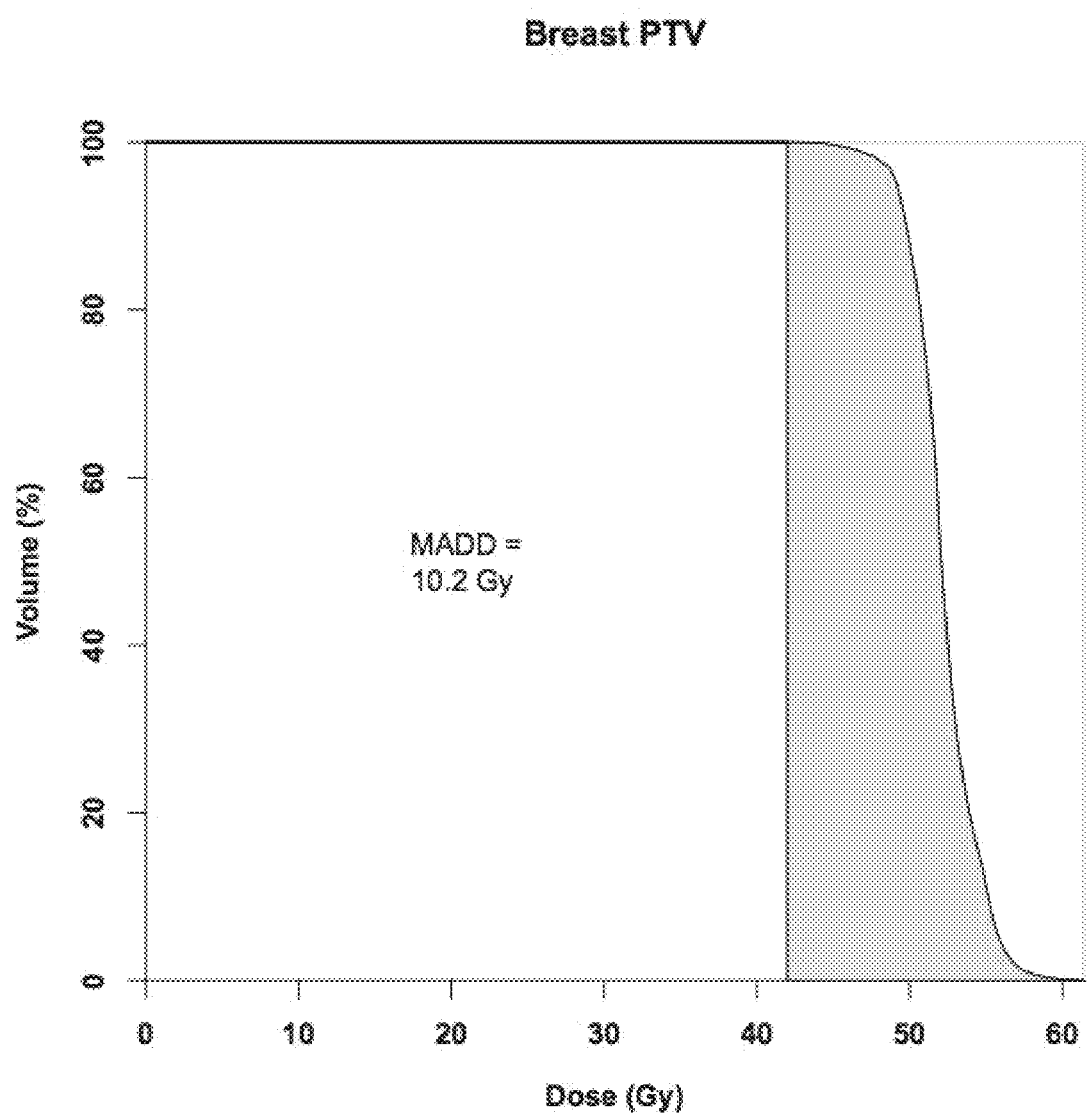
FIG. 5 shows the MADD for the breast PTV, where the prescribed dose was 42 Gy but the treatment plan also delivered a boost dose to the breast.

Moreover, the SD is defined with respect to the central measure, $\mu$. The SD cannot detect errors in the treatment planning prescription, regardless of the magnitude of the difference between the prescribed dose and the actual $\mu$. FIG. 5 shows a real case in which the MADD of the breast PTV was 10.2 Gy. Even without knowledge of the prescription, a deviation of that magnitude immediately raises a red flag. The prescription to the breast was 42 Gy with an integrated boost to 51 Gy, but the PTV assigned the boost dose to the breast. The SD showed an innocuous value of 1.8 Gy. Arguably, such huge error would not be missed in any review of a treatment plan. However, if a large error is undetectable with the SD, then the SD would be of no help when smaller errors between $\mu$ and the prescription occur and would thus escape notice. In contrast, the MADD can provide a safety warning.

Design of DVH Scores

The availability of the same metric for various structures allows the application of basic weight calculus. It would be straightforward to implement a weighted sum, S, to formalize the ranking attributed to each structure:

$$S = \sum_{j=1}^m w_j \times M_j(A_{ij}), \qquad (10)$$

where m is the total number of structures taken into consideration in a patient, $w_j$ is the relative importance attributed to structure j, j=1 . . . m, $A_{ij}$ is the dose reference matrix of the structure j for dose ranges $A_i$, and $M_j(A_{ij})$ is the MADD of the structure j. The choice of $w_j$ would depend on clinical factors and may be built on established recommendations.

Handling of Embedded Substructures

A practical issue currently gaining importance is the increased number of structures and substructures required in radiation treatment planning. Target volumes can be composed of several structures with different dose prescriptions, (e.g., breast cancer where the targets are the whole breast and the tumor bed boost, head and neck cancer with 3 target dose levels, the elective lymph nodes receiving a given dose, the high risk lymph nodes receiving a higher dose, and the macroscopic lymph nodes and primary tumor receiving a further dose). Organs at risk might have sub-regions assigned higher priority, such as the left anterior descending coronary relative to the heart. The MADD can handle effortlessly structures and embedded substructures. An example is shown in FIG. 4A-4F.

Interpretability of the MADD Metric

The demand for defining multiple structures has multiplied. The evaluation of treatment plans can be lost in the plurality of details comprising each plan. The MADD, in contrast, lends itself to a synthesis of how much a treatment plan diverts from prescription. FIG. 4A-4F shows how shading the MADDs within the DVHs maintained DVH information, while at the same time providing an overview of the dose deviations within structures and between structures, organs at risk, and target volumes.

Currently, reporting (and comparing) DVHs requires several tables of selected DVH values. Reading complex tables of dose points may be a hindrance considering the critical time constraint in reviewing and approving a treatment plan. As automated real-time adaptive planning become available, the need arises for an understandable tool providing an immediate evaluation of the treatment plan. Thus, the MADD metric can be a timely adjunct.

Limitations

Regarding target structures, the MADD makes no distinction of under dosage and over dosage. This is however not a real limitation. Treatment plans in general already penalize under dosages. Typically, 95% of a target volume would receive a dose in excess of the prescription (FIG. 4A-4F). Thus, the situation in which targets have high MADD values attributable to under dosage would be very unusual.

The DVH is a two-dimensional ("2D") representation of a three-dimensional ("3D") dose distribution. The MADD alone would further reduce the DVH to a single dimension. Hence, the MADD was integrated with the DVH as seen in FIG. 4A-4F. The definition of the MADD is an instance of the generalized mean absolute deviation. The statistical properties of the generalized absolute deviation have received scant attention.

Separating Excess and Insufficient Doses

In equations (1)-(10), the MADD makes no distinction of under or insufficient dosage and over or excess dosage. There might arise situations in which specific information on insufficient and excess dose would be useful, or in which the user might be interested only in one component. As an example, when the user wants to analyze the outcome of cancer patients who received radiation therapy, insufficient and excess dose information may be important. The focus might be on the rates of recurrences, in which case information on insufficient doses would be important. Conversely, the focus of the analysis might be on the rates of toxicities, in which case information on excess doses would be most needed. The present invention includes a decomposition of the MADD as discussed below.

An indicator function I is defined as shown below, where $$I(x > A) = \begin{cases} 0 & \text{if } x \leq A \\ 1 & \text{if } x > A \end{cases} \quad (11)$$

$$I(x \leq A) = \begin{cases} 1 & \text{if } x \leq A \\ 0 & \text{if } x > A \end{cases} \quad (12)$$

In this symbolic notation, both unsubscripted x and A refer to doses ranges. Combining equations (11) and (12), we get $$I(x>A)+I(x\leq A)=1 \quad (13)$$

Then, MADD M(A) can be written as shown below:

$$M(A) = M(A) \times 1 \quad (14)$$
$$= M(A) \times [I(x > A) + I(x \leq A)]$$
$$= [M(A) \times I(x > A)] + [M(A) \times I(x \leq A)]$$

In this way, the MADD is decomposed as the sum of the mean absolute deviation for which there is an excess dose (x>A), and the mean absolute deviation for which there is an insufficient dose (x<A), considering that the deviation is 0 when (x=A).

Using the decomposition of the MADD as shown in equation (14), it is then possible to evaluate excess and insufficient MADD. Thus, substituting equation (7) in equation (14), we get:

$$M(A)_{excess} = \sum_{i=1}^{n} \frac{I(x_i > A_i) \times |x_i - A_i| \times \delta y_i}{V_0} \quad (15)$$

$$M(A)_{insuff} = \sum_{i=1}^{n} \frac{I(x_i < A_i) \times |x_i - A_i| \times \delta y_i}{V_0} \quad (16)$$

Herein, $M(A)=M(A)_{excess}+M(A)_{insuff}$

Therefore, the computation provides the user with all values: the MADD, the MADD pertaining to excess dose, $M(A)_{excess}$, and the MADD pertaining to insufficient dose, $M(A)_{insuff}$.

Figure 8:
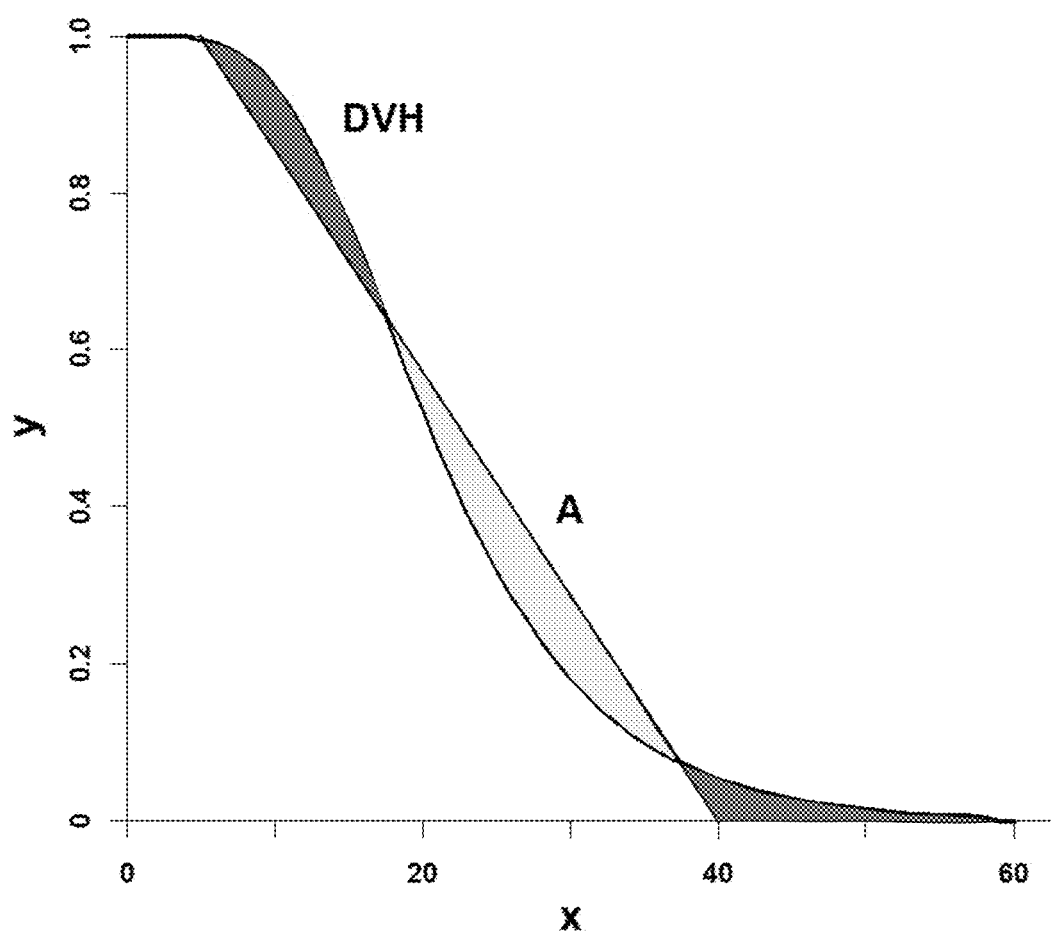
FIG. 8 shows the DVH for an organ at risk that receives a mean dose of 22.11 Gy, which is computed from the total area under the DVH curve.

FIG. 8 illustrates the application of MADD pertaining to a combination of insufficient and excess dose. The curve represents the DVH for an organ at risk. The mean dose received by the organ is 22.11 Gy, computed from the total area under the DVH curve. Because of proximity to a target, complete avoidance of the organ is not feasible. A tolerance dose to the organ ranging from 5 to 40 Gy has been considered acceptable. The oblique line A represents that dose range. The trapezoidal area under A represents a theoretical acceptable mean dose of 22.5 Gy. The actual mean organ dose appears below that limit. There is a mean absolute insufficient dose deviation MADDinsuff of 1.46 Gy computed from equation (16), shown as the light grey area in FIG. 8. However, the mean absolute excess dose deviation computed from equation (15), MADD excess, is 1.07 Gy, representing 4.8% beyond tolerance. The excess dose is shown as the dark grey shaded areas in FIG. 8.

CONCLUSION

The mean absolute dose deviation is a metric that can be advantageously applied to the analyses of dose-volume histograms. It provides a unified summary of the DVHs of organs at risk and of target structures. It can help to interpret the display of DVHs. The advantages of the MADD strongly support its systematic implementation and the need to evaluate it in prospective clinical trials.

The present invention generalizes the applicability of the MADD to more flexible reference dose. In addition, the decomposition of the MADD into distinct excess and insufficient dose components provides extended utility for clinical practice.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for enabling calibration of a dose delivery of a radiotherapy treatment plan, characterized in that the method comprises the steps of:
    (a) providing a dose-volume histogram (DVH) (100) of the treatment plan for a structure (300) with a volume $V_0$, and a reference dose A (20), the DVH comprising a plurality (n) of data points, each data point comprising a dose of radiation $x_i$(10) corresponding to a percentage of volume $\delta y_i$ (30);
    (b) determining a calibration parameter M(A) (110), based on the DVH (100), to quantify the dose delivery of the treatment plan, wherein the M(A) (110) is calculated using the following equation:

$$M(A) = \sum_{i=1}^{n} \frac{|x_i - A| \times \delta y_i}{V_0};$$

and
    (c) refining the treatment plan based on said calculated M(A) value;
    wherein the calibration of the treatment plan is separate from administration of the treatment plan to a patient.

2. The method of claim 1, wherein refining the treatment plan comprises:
    (a) comparing the M(A) to a reference value; and
    (b) revising the treatment plan when the M(A) is above the reference value, determining a new M(A) for the revised treatment plan, and (c) repeating steps a and b of refining the treatment plan until the calibration parameter is below the reference value.

3. The method of claim 1, wherein refining the treatment plan comprises:
    (a) searching for $A_{min}$ (150) by adjusting parameters of the treatment plan, wherein $M(A_{min})$ (140) is a minimum value.

4. The method of claim 1, wherein the method further comprises identifying an amount of insufficient dosage (125) by multiplying M(A) with a step function $I_{insufficient}$ (120), wherein:

$$I_{insufficient}(x) = \begin{cases} 1 & \text{if } x \leq A \\ 0 & \text{if } x > A \end{cases}.$$

5. The method of claim 1, wherein the method further comprises identifying an amount of excess dosage (135) by multiplying M(A) with a step function $I_{excess}$ (130), wherein:

$$I_{excess}(x) = \begin{cases} 0 & \text{if } x \leq A \\ 1 & \text{if } x > A \end{cases}.$$

6. A system (1) for enabling calibration of a radiation therapy treatment plan for a tumor (302) within a structure (300) of a patient, the system (1) comprising:
    (a) a treatment plan optimization computer (2) having:
        (i) a memory to store data; and
        (ii) treatment plan optimization software (3); and
    (b) an input device (4) in communication with the treatment plan optimization computer (2) and software (3) to provide user access to control functions of the treatment plan optimization software (3);
    (c) a graphical user interface to display an at least two-dimensional image slice (310) of a tumor target volume (311) and a non-target structure volume (312), graphical objects, and graphical representations of radiation dose distribution calculated for each iteration of a proposed dose and radiation beam arrangement overlaid upon the displayed image slice
    wherein the treatment plan optimization software (3) comprises a set of instructions that, when executed by the treatment plan optimization computer (2), causes the computer to perform operations to computationally obtain the proposed radiation dose and beam arrangement (5) and to computationally iteratively optimize the proposed radiation dose in the beam arrangement based on a plurality of constraints to form the optimized radiation dose and beam arrangement, wherein the determination of the optimal dose is separate from administration of the radiation therapy treatment plan using the optimal dose,
    wherein the operations comprise:
        (a) receiving inputs from the input device (4) representing direct graphical user manipulation of a graphical representation of radiation dose distribution for a current iteration of the proposed radiation dose and beam arrangement (5) displayed on the graphical user interface, and responsive to user manipulation of the displayed graphical representation of radiation dose distribution for the current iteration of the proposed radiation dose and beam arrangement; and
        (b) computationally obtaining and providing data to graphically display a graphical representation of radiation dose distribution for a next iteration of the proposed radiation dose and beam arrangement which substantially realizes the graphically altered radiation dose distribution, to thereby iteratively form the optimized radiation dose and beam arrangement,
wherein the operation of computationally obtaining and providing data comprises:
(a) obtaining a dose-volume histogram (DVH) (100) of the structure (300) from a computerized "Treatment Planning System" (TPS) (6),
(b) providing a mean absolute dose deviation (MADD) (110) based on the (DVH) (100), wherein the MADD (110), or M(A), is calculated using the following equation:

$$M(A) = \sum_{i=1}^{n} \frac{|x_i - A| \times \delta y_i}{V_0}$$

wherein $x_i$ (10) is a dose corresponding to a percentage of volume $\delta y_i$ (30), A is a reference dose (20), $V_0$ is the volume of interested structure, and the calculation process is done by a computer with an input dose of A;
(a) identifying an amount of insufficient dosage (125) by multiplying M(A) with a step function $I_{insufficient}$ (120), wherein:

$$I_{insufficient}(x) = \begin{cases} 1 & \text{if } x \leq A \\ 0 & \text{if } x > A \end{cases}$$

(b) identifying an amount of excess dosage (135) by multiplying M(A) with a step function $I_{excess}$ (130), wherein:

$$I_{excess}(x) = \begin{cases} 0 & \text{if } x \leq A \\ 1 & \text{if } x > A \end{cases},$$

and
(c) finding an applicable dose $A_{min}$ (150) for the DVH (100) by searching for $A_{min}$ wherein $M(A_{min})$ (140) reaches minimum value for the DVH (100).

7. The system of claim 6, wherein the operation of finding $A_{min}$ comprises:
(a) obtaining a series of DVH(j) by adjusting parameters for DVH (100) for the structure (300) of the patient, wherein j is at least 1;
(b) finding a series of applicable dose $A_{min}$ (j) (150) by calculating a series (j) of $M(A_{min})$ (j) (140) for each DVH(j); and
(c) identifying an optimal dose $A_0$ (160) that has minimum standard deviation (SD) for a series of applicable dose (150) from the obtained $M(A_{min})$ (j) (140), wherein the optimal dose $A_0$ (160) is the base for an optimal treatment plan for the tumor (302) in the radiation therapy, or the least amount of radiation received by an at-risk organ (301) when the structure (300) is under treatment.

8. The system of claim 6, wherein all dose points of the specified dose range are input by a user.

9. The system of claim 6, wherein two or more dose points of the specified range are input by a user, and remaining dose points of the specified range are computed using interpolation.

10. The system of claim 6, wherein the structure of interest is a target volume of tumor or an organ at risk.

11. The system of claim 10, wherein the specified reference dose is zero when the structure of interest is an organ at risk.

12. The system of claim 6, wherein a partial volume is a percentage of the total volume of the structure of interest.

13. The system of claim 6, wherein a partial volume is a relative proportion of the total volume of the structure of interest.

14. The system of claim 6, wherein the insufficient dose and the excess dose are indiscriminately combined to obtain the total mean absolute dose deviation.

\* \* \* \* \*